(12) United States Patent
Mueller et al.

(10) Patent No.: US 7,311,720 B2
(45) Date of Patent: Dec. 25, 2007

(54) CLOSURE DEVICE FOR A PUNCTURE CHANNEL AND APPLICATOR DEVICE

(75) Inventors: Gottfried Mueller, Igersheim (DE); Thomas Beck, Durchhausen (DE); Manfred Dworschak, Duerbheim (DE); Sven Eggerstedt, Hamburg (DE)

(73) Assignee: Aesculap AG & Co. KG, Tuttlingen (DE)

( * ) Notice: Subject to any disclaimer, the term of this patent is extended or adjusted under 35 U.S.C. 154(b) by 415 days.

(21) Appl. No.: 10/789,372

(22) Filed: Feb. 26, 2004

(65) Prior Publication Data

US 2004/0220592 A1 Nov. 4, 2004

(30) Foreign Application Priority Data

Mar. 6, 2003 (DE) ................ 103 10 995

(51) Int. Cl.
*A61B 17/08* (2006.01)
*A61B 17/04* (2006.01)

(52) U.S. Cl. ............... 606/213; 606/151; 606/232; 606/215; 606/200; 606/198; 606/95

(58) Field of Classification Search ........... 606/151, 606/185, 213, 232, 215, 200, 198, 95
See application file for complete search history.

(56) References Cited

U.S. PATENT DOCUMENTS

| 3,397,699 | A | * | 8/1968 | Kohl ............... 604/105 |
|---|---|---|---|---|
| 3,874,388 | A | * | 4/1975 | King et al. ............ 606/232 |
| 4,276,659 | A | * | 7/1981 | Hardinge ............ 606/95 |
| 5,053,046 | A | * | 10/1991 | Janese ............ 606/215 |
| 5,192,301 | A | | 3/1993 | Kamiya et al. |
| 5,397,331 | A | * | 3/1995 | Himpens et al. ............ 606/151 |
| 5,545,178 | A | | 8/1996 | Kensey et al. |
| 5,853,422 | A | | 12/1998 | Huebsch et al. |
| 5,944,730 | A | | 8/1999 | Nobles et al. |
| 6,197,041 | B1 | * | 3/2001 | Shichman et al. ........ 606/185 |
| 6,613,070 | B2 | * | 9/2003 | Redmond et al. ........ 606/213 |
| 6,616,685 | B2 | * | 9/2003 | Rousseau ............ 606/213 |
| 7,052,516 | B2 | * | 5/2006 | Cauthen et al. ........ 623/17.16 |
| 2002/0026094 | A1 | | 2/2002 | Roth |

FOREIGN PATENT DOCUMENTS

| DE | 100 27 186 | 12/2001 |
|---|---|---|
| EP | 0 544 485 | 6/1993 |
| WO | 95/29635 | 11/1995 |

* cited by examiner

*Primary Examiner*—Michael J. Hayes
*Assistant Examiner*—Katherine Dowe
(74) *Attorney, Agent, or Firm*—Lipsitz & McAllister LLC

(57) ABSTRACT

In a closure device for an opening in a layer of tissue comprising a plurality of wings which provide and/or hold bearing areas on tissue surrounding the opening, the wings are held by means of respective joints for swivelling movement on a base part.

28 Claims, 5 Drawing Sheets

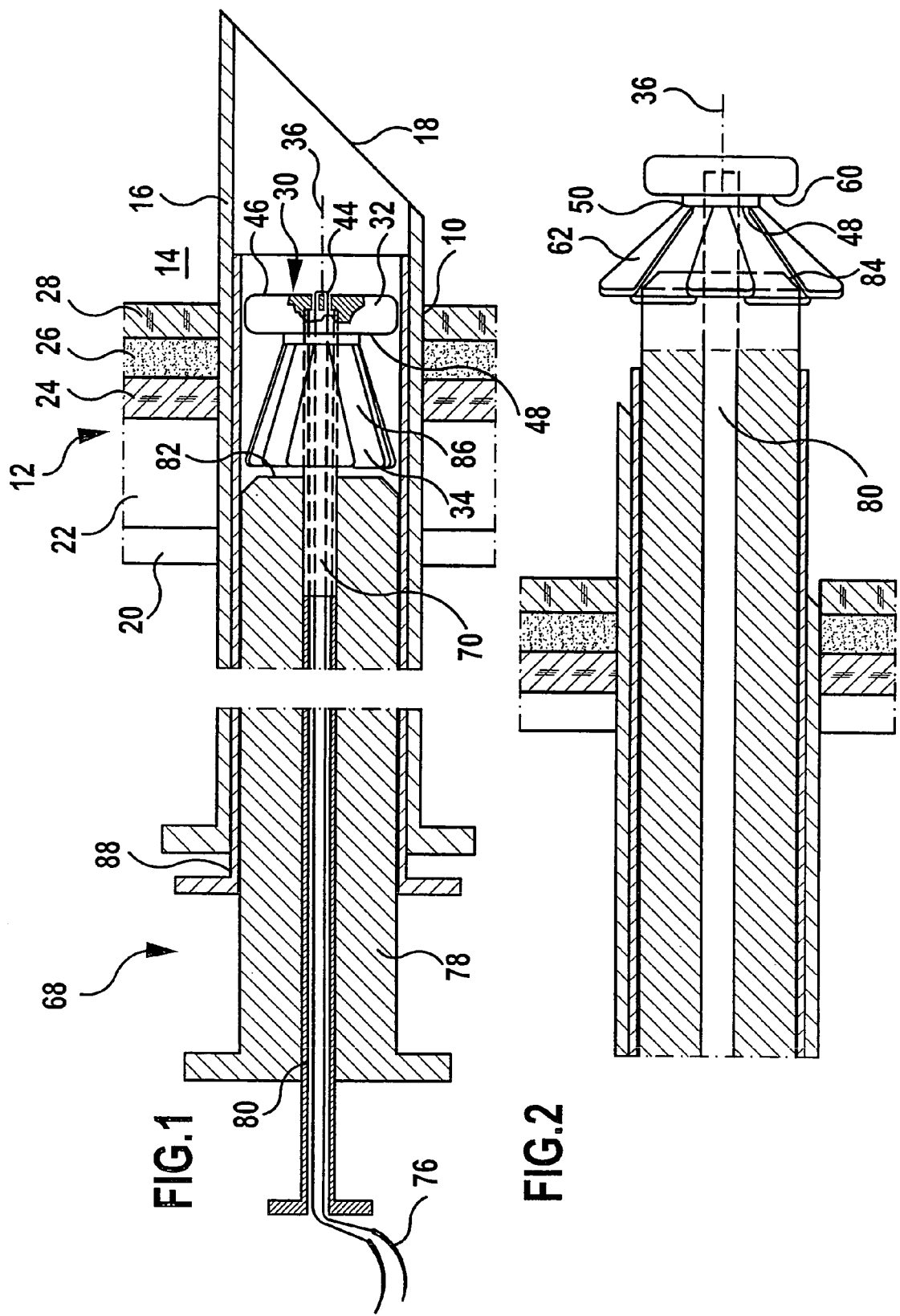

FIG.3
FIG.4
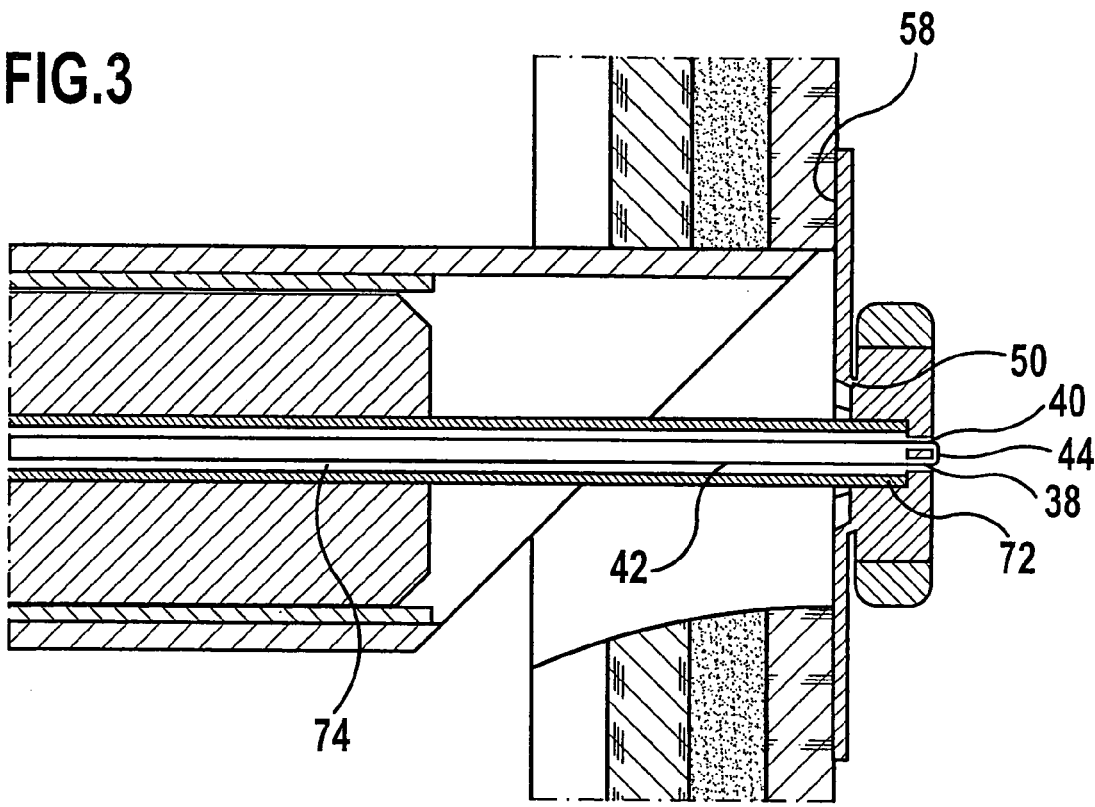
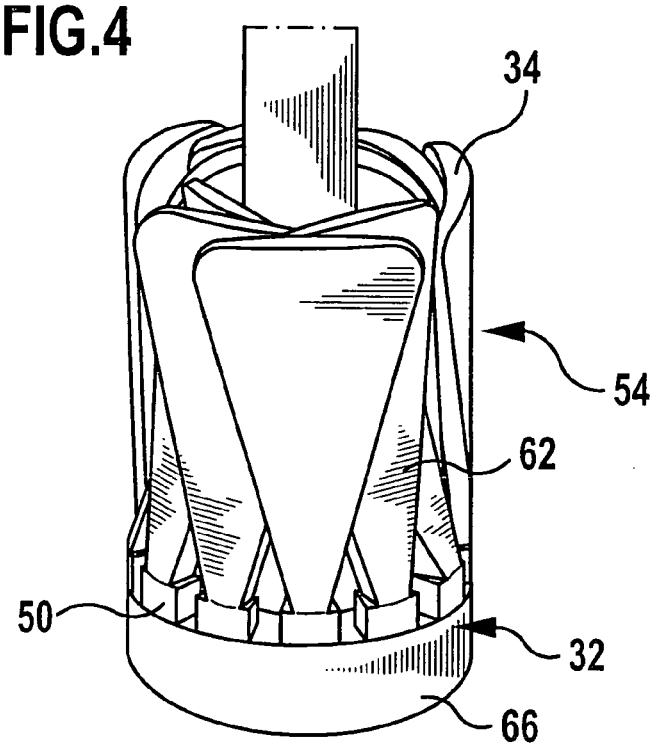

CLOSURE DEVICE FOR A PUNCTURE CHANNEL AND APPLICATOR DEVICE

The present disclosure relates to the subject matter disclosed in German application No. 103 10 995.1 of Mar. 6, 2003, which is incorporated herein by reference in its entirety and for all purposes.

BACKGROUND OF THE INVENTION

The invention relates to a closure device for an opening in a layer of tissue, comprising a plurality of wings which provide and/or hold bearing areas on tissue surrounding the opening.

The invention further relates to an applicator device for such a closure device.

From DE 100 27 186 A1 a device is known for closing a puncture channel in a layer of tissue with a surgical suture thread, which comprises a flat foldable bearing element which the suture thread engages in such a way that when tension is applied to the suture thread running through the puncture channel of the layer of tissue, the bearing element unfolds and positions itself flat against the edge of the puncture channel.

From U.S. Pat. No. 5,053,046 A a closure element is known, in particular, in conjunction with sealing puncture channels in the spinal chord, which comprises a holding cone on which wings are seated. The wings are made of an elastic material and owning to their intrinsic opening elasticity are able to spread outwardly.

Closure devices for openings in tissue are also known from WO 95/29635 A1 or from U.S. Pat. No. 5,944,730 A.

SUMMARY OF THE INVENTION

In accordance with the present invention, a closure device is provided which is easy for an operator to insert. This is achieved by wings that are held by means of respective joints for swivelling movement on a base part.

Owing to the fact that in accordance with the invention the wings are held by means of respective joints so as to be capable of swivelling movement, a bearing position can be reached in a simple way, in which the wings or bearing elements held by the wings are made to bear against the tissue. A swivelled-in position is, however, also achievable in a simple way, in which the transverse dimensions of the closure device are minimized so that it is insertable through the puncture channel and, in particular, through a trocar sheath into a corresponding body cavity in order to position the wings against the tissue.

Transfer between the swivelled-in position and the flapped-out bearing position can be achieved in a simple way.

The base part can then be designed so as to be introducible in a defined way, for example, through a trocar sheath, in particular, so as to avoid canting. An operator can thus position the closure device in a simple way. This is also possible without optical checking.

Such a closure device can be manufactured in a simple way by, for example, the joints being constructed by means of film hinges.

It is particularly advantageous for the joints to be hinged joints. Such hinged joints have a single swivel axis. In the inventive closure device a single swivel axis is sufficient because the wings need only be transferred from a swivelled-in position in which the outer transverse dimensions of the closure device are minimized, into a bearing position in which the closure device can be placed with the wings against the tissue.

Such hinged joints can be manufactured in a simple way as film hinges. A film hinge is characterized by a thinning of material in the area in which the swivelling capability must be ensured.

In particular, swivel axes of the joints are oriented substantially at a right angle to a central axis of the base part. Minimization of the outer transverse dimensions of the closure device is thus achievable in a simple way by swivel movement being directed towards the central axis. Furthermore, a large bearing area is made available over the wings by swivel movement outwardly away from the central axis.

It is also expedient for the swivel axes of the joints to lie parallel to tangents to an outer circumference of the base part. Maximization of the bearing area of the closure device on the tissue is thus achievable when the wings are swivelled outwards, i.e., lie in a bearing position. The wings may, for example, be of circular sector design so that the intermediate area between spaced wings is minimized, which, in turn, allows the bearing area to be maximized when the wings are swivelled out.

The inventive closure device can be manufactured in a simple way when the wings are integrally held on the base part. In particular, no shafts or the like then need be provided for construction of the joints.

Provision may be made for wings outside of the associated joints to be of essentially rigid design. A defined, stable and substantially rigid bearing area for the closure device to bear on the tissue is thereby provided.

Provision may also be made for the wings to hold bearing elements made of a bendable material. In particular, a bearing element is then held taut between adjacent wings. The bearing element may, for example, be held in the fashion of a film hinge on a wing, with a wing being, in particular, of ridge-shaped design. A bearing area which is interruption-free can thus be provided. With appropriate arrangement of the bearing elements on the wings, a continuous smooth bearing area can also be provided in the flapped-out position so that, for example, tissue is prevented from growing into spaces between wings. The bearing elements may be seated, for example, in the fashion of film hinges on the wings.

Owing to the bendable design of the bearing elements, these are folded in the flapped-in position, with areas of the bearing elements lying over one another. Consequently, the bearing elements do not protrude over the outer circumference of the base part in the flapped-in position, whereas the bearing areas can be spread out during transition to the flapped-out position. The transition from the flapped-in position to the flapped-out position is similar to the opening-up of an umbrella.

It is advantageous for the base part outside of the joints to be of substantially rigid design. Such a closure device is also easy to manufacture.

The inventive closure device can be introduced in a simple way into a body cavity, for example, by means of a trocar sheath when the wings are arranged for swivel movement on the base part such that in a flapped-in position they do not protrude laterally over the base part. The outer dimensions of the closure device are then determined in the flapped-in position by the outer dimensions of the base part. The closure device can then be inserted, in particular, without canting, through the trocar sheath, into the body cavity.

Furthermore, it is expedient for the wings to form and/or hold bearing areas on the tissue in a flapped-out position.

For a defined position of the wings when bearing on the tissue, it is expedient for these to be oriented substantially at a right angle to a central axis of the base part in the flapped-out position. A stable bearing position is thus achievable with, for example, the closure device being prevented from being drawn into the puncture channel after removal of the trocar sheath. Even when very strong tension is applied to the suture material to suture the closure device to the tissue, it is ensured that the wings will remain in a horizontal plane and not be drawn into the trocar incision.

To achieve easy insertability of the closure device, for example, through a trocar sheath into a body cavity, in particular, the joints are set back on the base part in relation to a circumferential rim of the base part. A flapped-in position in which the wings do not protrude over the circumferential rim can thereby be established. The joints can then also be arranged such that in the flapped-in position the wings are, for example, arranged in the fashion of a fan so as to provide a large number of wings capable of swivelling movement, which make available a large bearing area.

Furthermore, it is expedient for the joints to be seated on an upper side of the base part, which faces the tissue when the bearing areas bear on the tissue.

It is thereby ensured that in a bearing position (the flapped-out position) the wings form a substantially horizontal plane over which the base part does not protrude. The base part or part of the base part is thus unable to enter the puncture channel and prevent the puncture channel from growing together.

To obtain a large bearing area it is advantageous for at least two wings to be provided. In particular, diametrically opposed wings are provided to avoid canting.

It is then particularly advantageous for the wings to be arranged around the circumference of the base part so as to avoid canting in any direction and to provide a large bearing area.

Provision is made for the base part to have a round outer cross section. It is then easily insertable through a trocar sheath into a body cavity so as to subsequently close the puncture channel in which the trocar sheath is seated.

It is particularly advantageous for a suture thread to be held on the base part. The closure device can be sutured to the tissue with this suture thread so as to hold the closure device securely and achieve closure of the puncture channel (the opening in the tissue).

In particular, the base part comprises spaced openings for passage of a suture thread therethrough. The suture thread can be looped through these openings, and a bearing area for the suture thread is simultaneously provided between the openings on the base part. By means of this bearing area with the suture thread looped therethrough, the base part can then be drawn against the tissue so as to ensure secure fixing thereof.

Provision may be made for the wings to extend at an incline to the base part in a flapped-in position. This results in a hollow cone-like space in which an opening instrument can engage so as to unfold the wings and transfer them into the flapped-out position. Introduction of such an instrument is facilitated when the wings are at an incline to the base part. Provision may be made for the wings to stand at an incline in the flapped-in position by virtue of the design of the joints. It may, however, also be that the flapped-in position is a position in which the wings unfold by themselves from a substantially parallel position (in relation to the central axis of the base part) until they strike a surrounding wall, for example, the wall of a trocar sheath and cannot unfold any further. In this flapped-in position, too, (in relation to the flapped-out position in which the wings provide bearing areas for the tissue) the closure device is also insertable through a puncture channel into a body cavity.

It is particularly advantageous for the base part to provide one or a plurality of bearing areas for the wings, which impede swivel movement of the wings beyond a bearing position. A defined bearing position is thus created, and this bearing position is also stabilized by means of the bearing areas on the base part. In particular, by means of the bearing area or bearing areas on the base part, the wings of the implant can be prevented from swivelling too far. It is, in turn, thereby ensured that even when strong tension is applied to the suture material, the wings of the implant will remain in the corresponding bearing plane and, in particular, the closure device will not be drawn with its base part into the puncture channel.

For example, the bearing area or surfaces are formed on a ring-shaped bearing element which, in particular, is part of the base part. The bearing area can thus be manufactured in a simple way.

Provision may also be made for the wings to comprise a support for bearing on the associated bearing areas. This support extends, for example, in a longitudinal direction of the wings. With such a support, a greater distance can be created between the joint and the bearing area, so that, for example, an improved swivelling capability can be achieved or the joints can be manufactured in a simpler way.

It is expedient for the wings to have a width which increases in the direction away from the base part and to comprise, for example, an outer rim in the shape of a ring sector. The wings can then be arranged around a circular base part without protruding laterally over this (in the flapped-in position). In the flapped-in position, they can then be positioned so as to be arranged around a central axis of the base part. As they unfold, a large bearing area is made available, which has gaps owing to the spacing between adjacent wings, but the expanse of these gaps is minimal.

It is expedient for the base part to be provided with a coupling for a holding mandrel. Such a holding mandrel can be inserted as navigation instrument so as to position the inventive closure device on the tissue. By virtue of the inventive design of the closure device with base part and wings, the closure device can be inserted (in the flapped-in position) by means of the holding mandrel into the body cavity without any necessity for an optical check.

Provision may be made for the base part to comprise a holding element for the wings and a ring element. The wings are seated on the holding element. The ring element constitutes the bearing areas for preventing the wings from swivelling beyond the bearing position.

Such a closure device can be manufactured in a simple way when the ring element is held in the fashion of a snap closure on the holding element. The ring element can then be fixed in a simple way on the holding element, with a secure connection being ensured between ring element and holding element after the fixing.

Also, in accordance with the invention an applicator device is provided with which a closure device in accordance with the invention can be positioned in a simple and secure way.

This is accomplished with a positioning element which is longitudinally displaceable in the trocar sheath is provided, by means of which the wings of the closure device are transferable from a flapped-in position in which the closure device is displaceable in a trocar sheath to a flapped-out position.

The positioning element serves to unfold the wings, i.e. to move them into the bearing position. There is then no necessity for provision of intrinsic elasticity of the joints, i.e., no intrinsic unfolding of the wings need be provided. The closure device can be positioned without any optical adjusting aids by providing a longitudinally displaceable positioning element.

In particular, the positioning element has bearing areas for the wings for swivelling these outwardly.

Furthermore, it is advantageous for a holding mandrel for holding or positioning the closure device to be provided. This holding mandrel serves to navigate the closure device when inserting it into the body cavity and fixing it on the tissue.

It is then particularly advantageous for the positioning element to at least partially surround the holding mandrel. It is thus possible to actuate positioning element and holding mandrel separately. For example, the positioning element is not necessary when inserting the closure device into a body cavity, but only when the wings are to be opened. If the positioning element surrounds the holding mandrel, the holding mandrel can then move without being impeded in the trocar sheath.

It is then particularly advantageous for the holding mandrel to be guided for longitudinal displacement on the positioning element. The positioning element itself then provides the guidance, in particular, by means of a guide channel, for the holding mandrel. A secure positioning of the closure element, in particular, with minimization of transverse movements, is thereby achievable.

It is then particularly advantageous for the positioning element to provide a centering means for the holding mandrel so that the closure device can be inserted into the body cavity and unfolded there without any optical adjusting aids.

Furthermore, it is expedient for a suture thread to be guided through the holding mandrel. The closure device can thereby be pressed by means of the suture thread against the tissue with a minimization of tension forces transversely to the central axis of the base part.

It is particularly advantageous for a reducing sleeve or a set of reducing sleeves to be provided for positioning the positioning element. These reducing sleeves fill out the space between an interior of the trocar sheath and the positioning element. Due to the reducing sleeves, a given closure device can also be positioned with an associated positioning element when the diameter of the trocar sheath differs. A centering of the positioning element and hence of the closure device during insertion through the trocar sheath is simultaneously achievable. It is thus possible to dispense with optical adjusting aids when fixing the closure device to the tissue.

The following description of preferred embodiments serves in conjunction with the drawings to explain the invention in greater detail.

BRIEF DESCRIPTION OF THE DRAWINGS

FIG. 1 is a schematic sectional view of an embodiment of an inventive applicator device when inserting an embodiment of an inventive closure device;

FIG. 2 shows the applicator device according to FIG. 1, with the closure device positioned in a body cavity and wings of the closure device unfolded;

FIG. 3 shows the applicator device according to FIG. 1 with flapped-out wings of the closure device resting against the tissue delimiting the body cavity;

FIG. 4 is a schematic illustration of an embodiment of an inventive closure device with the wings in a flapped-in position;

DETAILED DESCRIPTION OF THE INVENTION

Figure 5:
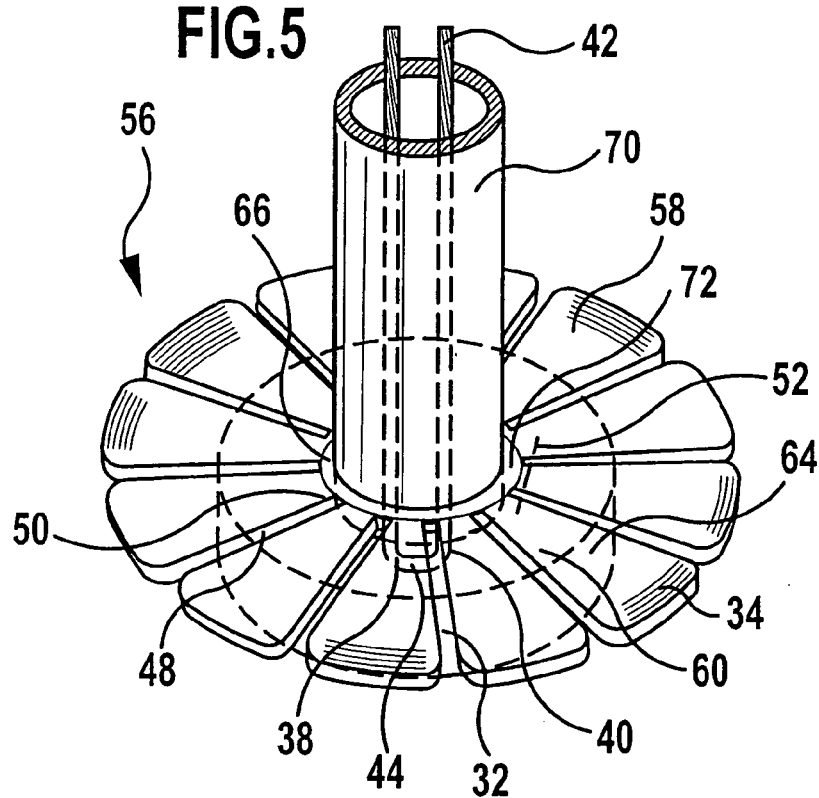
FIG. 5 shows the closure device according to FIG. 4 with flapped-out wings.

Inventive closure devices are used for closing openings and, in particular, puncture channels 10 in a layer of tissue 12. The layer of tissue 12 delimits a body cavity 14 such as, for example, the abdominal cavity.

Seated in the puncture channel 10 of the layer of tissue 12 is a trocar sheath 16 with a pointed end 18. The layer of tissue 12 surrounding the puncture channel 10 includes in the case of the abdominal cavity as body cavity 14 an epidermis layer 20, a fatty layer 22, a muscular layer 24, the fascia 26 and the peritoneum 28.

An embodiment of an inventive closure device generally designated 30 in FIG. 1 comprises a base part 32 on which a plurality of wings 34 are seated (FIGS. 4, 5). The base part 32 has a circular outer cross section with a central (center point) axis 36. Parallel to this central axis 36, two openings 38, 40 spaced from one another are formed in the base part 32 (FIG. 3) in offset relation to the central axis 36. A suture thread 42 is threaded through these openings 38, 40, and when tension is applied to the suture thread 42, a suture thread portion 44 lies against an underside 46 of the base part 32. The underside of the base part 46 has a substantially flat surface and may be provided with a depression for the suture thread portion 44, so that the suture thread does not protrude over this flat surface or is at least countersunk.

The wings 34 are seated on an upper side 48 of the base part 32 opposite the underside 46 and held thereon for swivelling movement. Allocated to each wing 34 is a hinged joint 50 as swivel joint, which may, for example, be a film hinge, to ensure swivelling movability of the wings 34. A swivel axis 52 (FIG. 5) is oriented transversely and, in particular, at a right angle to the central axis 36 of the base part. The swivel axes 52 run parallel to the corresponding tangent to the outer circumference of the base part 32. The hinged joints 50 are set back in relation to an outer circumference of the base part 32 to such an extent that in a flapped-in position 54 (FIG. 4) of the wings 34, in which the wings 34 are swivelled away from the upper side 48, the wings do not protrude over the outer circumference of the base part 32, so that the lateral dimensions of the closure device 30 are determined by the base part 32.

In a flapped-out position 56 (FIGS. 3, 5) the wings 34 are swivelled towards the upper side 48 and lie, in particular, at a right angle to the central axis 36.

The wings 34 thereby provide bearing areas 58 by means of which the closure device 30 can be placed against the tissue surrounding the puncture channel (against the peritoneum 28 in the embodiment shown), in order to thus close off this opening in the layer of tissue 12 from the outside.

The wings 34 are arranged around the central axis 36. At least two wings 34 and, preferably, such a number of wings 34 are provided that as large a bearing area as possible is made available to lie against the layer of tissue 12. In particular, diametrically opposed wings 34 are provided.

As shown in FIG. 5, the wings 34 themselves are of such shape that they have a width cross section which increases in the direction away from the base part. The wings 34 are thus of at least approximately circular sector shape. A large bearing area for placement against the layer of tissue 12 can thereby be made available. It is thus also possible to ensure in the flapped-in position 54 (FIG. 4) that the wings 34 do not protrude beyond the outer circumference of the base part 32.

The base part 32 provides an, in particular, ring-shaped bearing area 60 for the wings 34, which blocks further swivelling movement of the wings 34 when a side 62 (located opposite the bearing area 58) of the wings 34 facing the upper side 48 rests against the bearing area 60. The bearing area 60 is preferably formed on a ring element 64 (FIG. 6), which surrounds a holding element 66 of the base part 32, and the holding element 66, in turn, holds the wings 34 for swivelling movement by means of the hinged joints 50.

The bearing area 60 of the ring element 64 is preferably designed such that in the flapped-out position 56 the wings are oriented substantially at a right angle to the central axis 36 of the base part 32. In this way the wings 34 can lie flat on the layer of tissue 12.

As shown in FIG. 1, provision may be made for the wings 34 in the flapped-in position 54 to be oriented at an angle to the central axis 36, i.e., to be oriented at an incline thereto. As will be explained hereinbelow in further detail, transfer from the flapped-in position 54 to the flapped-out position 56 of the wings 34 is thus achievable in a simple way by means of an applicator device.

The inventive closure device 30 is positionable by means of an inventive applicator device, an embodiment of which is generally designated 68 in FIGS. 1 to 3. The applicator device 68 comprises a holding mandrel 70 for this purpose. The base part 32 has a coupling 72 for this holding mandrel 70 (FIGS. 3, 5) on the holding element 66. The base part 32 is fixable on the holding mandrel 70 by means of this coupling 72. The closure device can thus be navigated by means of the holding mandrel 70 for placement on the layer of tissue 12.

The holding mandrel 70 has a hollow interior 74 through which the suture thread 42 is guided outwards. After positioning of the closure device 30 on the layer of tissue 12 and removal of the trocar sheath 16 from the puncture channel 10, the closure device 30 can then be sutured to the layer of tissue 12 using needles 76.

The holding mandrel 70 is guided for longitudinal displacement in a positioning element 78. For this purpose, the positioning element 78 has a longitudinal channel 80 whose internal diameter is adapted to an external diameter of the holding mandrel 70. The holding mandrel 70 can thereby also be centered in the positioning element 78 so as to inhibit its transverse movability relative to the positioning element 78.

The positioning element 78, in turn, is displaceably guided in the trocar sheath 16 so that when displaced accordingly it can act upon the wings 34 in their flapped-in position 24 to bring about the flapped-out position 56.

For this purpose, the positioning element 78 has at its distal end 82 a frustoconical rim 84. The positioning element 78 itself preferably has a cylindrical external shape. The frustoconical rim 84 is adapted to an opening width of the wings 34 in the flapped-in position 54. The distal end 82 can thereby be pushed into a fan space 86 of the closure device 30 without abutting against the wings 34. If, however, the positioning element 78 is pushed further in the direction of the base part 32, which is held by the holding mandrel 70, the wings 34 can thereby be swivelled in the direction of the underside 46 so as to bring about the flapped-out position 56, insofar as the swivelling movability of the wings 34 is not blocked.

A set of reducing sleeves may be provided to enable adaptation of the applicator device 68 with the closure device 30 to trocar sheaths 16 of a predetermined diameter, in which case a reducing sleeve is inserted into the trocar sheath 16. The positioning element 78 is then inserted into the reducing sleeve 88, with the external diameter of the positioning element 78 being adapted to the internal diameter of the reducing sleeve 88. In turn, the positioning element 78 can thereby be centered in the trocar sheath 16, i.e., transverse movement of the positioning element 78 in the trocar sheath 16 can be blocked. The reducing sleeve 88 thus substantially fills out the space between the positioning element 78 and the trocar sheath 16 if the positioning element 78 has a smaller external diameter than the internal diameter of the trocar sheath 16.

The inventive applicator device 68 and the inventive closure device 30 operate as follows:

The closure device 30 is fixed by means of its base part 32 on the holding mandrel 70. The suture thread 44 which extends through the interior 74 of the holding mandrel 70 is held on the base part 32. The needles 76 sit at the end of the suture thread 44. The holding mandrel 70 is arranged within the positioning element 78. The applicator device 68 with the closure device 30 held thereon is inserted into the trocar sheath 16, with the wings 34 in the flapped-in position 54, i.e., they do not protrude beyond the outer circumference of the base part 32, so that the closure device 30 is displaceable by means of the applicator device 68 in the trocar sheath 16.

The closure device 30 is then pushed so far into the body cavity 14 that the wings 34 can be transferred from the flapped-in position 54 into the flapped-out position 56. The swivelling movement is brought about by the positioning element 78 which is pushed in the direction of the base part. The distal end 82 of the positioning element 78 acts upon the wings 34 and causes them to swivel towards the underside 46 of the base part 32. The flapped-out position 56 is reached by the wings 34 bearing on the bearing area 60 of the ring element 64. The trocar sheath 16 and the positioning element 78 are then retracted until the wings 34 bear with their bearing areas 58 on the layer of tissue 12. The applicator device 68 and the trocar sheath 16 can then be removed from the puncture channel 10.

The holding mandrel 70 and the positioning element 78 are preferably provided with longitudinal openings for threading out the suture thread 42.

After removal of the trocar sheath 16, only the suture thread 42 for which, for example, double reinforced suture material is used, remains in the puncture channel 10. The puncture channel 10 closes, and by applying tension to the suture thread 42 the puncture channel is covered on the inside, i.e., at the body cavity 14, by the closure device 30. The closure device 30 is thus made to bear on the layer of tissue 12 by the application of tension. In this position, for example, ends of the suture thread 42 are knotted, and the knot thus formed is located in the fatty layer 22 underneath the epidermis layer 20. The ends are then knotted on the outside by outwardly puncturing the fatty layer 22 and the epidermis layer 20 using the needles 76, so that the upper portion of the fatty layer 22 and the epidermis layer 20 are drawn together. The puncture channel 10 is thereby also closed on the outside.

During passage of the closure device 30 into the body cavity 14, the wings 34 may already unfold, with the final flapped-out position 56 being brought about by the positioning element 78. With the aid of the holding mandrel 70, the closure device 30 can be navigated as implant exactly onto the puncture channel 10, i.e., the trocar incision. As the closure device 30 is adapted by means of its base part 32 to the puncture channel 10 by the interior of the trocar sheath 16 and is centered in the trocar sheath 16, the opening 10 in the layer of tissue 12 can be completely covered.

The area of the hinged joints 50 and that area of the wings 34 which is connected to the hinged joints 50 or on which the hinged joints 50 are formed are stabilized by means of the bearing area 60 of the ring element 64. It is thereby ensured that in the event of strong tension on the suture thread 42 the closure device 30 will nevertheless remain in a position in which the wings 34 are oriented substantially at a right angle to the central axis 36 of the base part 32. In particular, the closure device 30 is prevented from being drawn into the puncture channel 10.

Due to the centering of the closure device 30 in the trocar sheath 16 by means of the inventive applicator device 68, the arrangement of the wings 34 for swivelling movement on the closure device 30 and, in particular, the provision of the bearing area 60, there is no need to optically check whether the closure device 30 is positioned such that it bears on the layer of tissue 12.

The wings 34 are preferably held integrally on the base part 32.

Figure 6:
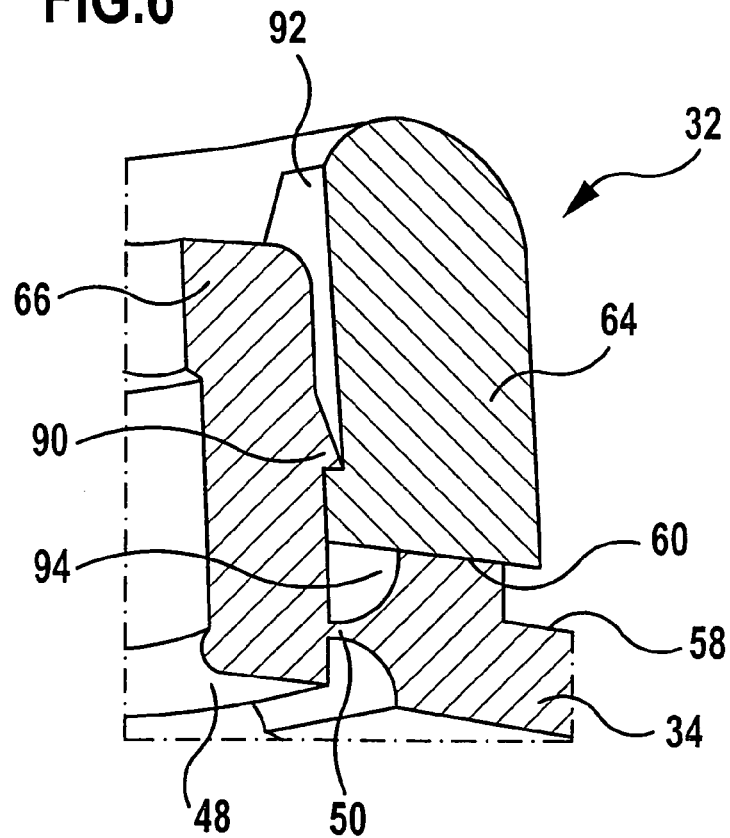
FIG. 6 is a partial sectional view of an embodiment of a base part holding wings.

In the embodiment of a base part 32 shown in FIG. 6, the wings 34 are integrally seated by means of respective film hinges as hinged joints 50 on the holding element 66. The ring element 64 is a separate element which surrounds the holding element 66. The holding element 66 has noses 90 distributed over its circumference, and the ring element 64 is held in the fashion of a snap closure on the holding element 66. For this purpose, the ring element 64 has corresponding recesses 92 in which the noses 90 are insertable. The holding element 66 and/or the ring element 64 are of such appropriate elastic design that these noses 90 are able to dip into the recesses 92 in order to fix these two elements 64 and 66 to one another. Disengagement by way of the noses 90 is inhibited.

The base part 32 is otherwise of essentially rigid design outside of the hinged joint 50. The wings 34 are also of essentially rigid design outside of the hinged joint so that movability of the wings 34 relative to the base part 32 is only permitted by means of the hinged joints 50.

The hinged joints 50 are formed by a thinning of material: An end 94 of the wings 34 facing the holding element 66 has a certain width. In the area of the hinged joint 50, the respective wing 34 narrows at the transition to the holding element 66.

Figure 7:
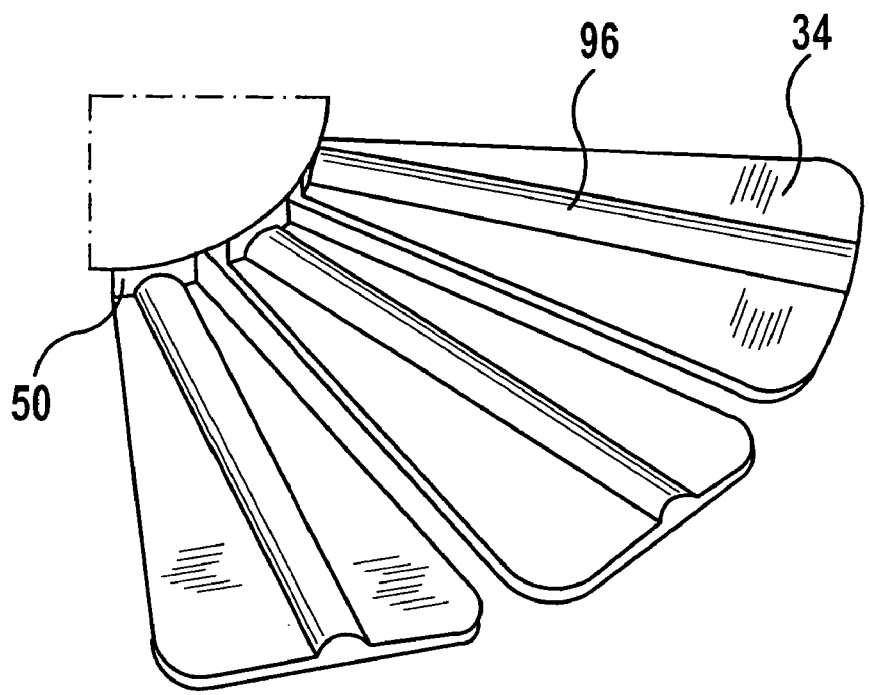
FIG. 7 shows an embodiment of wings.

As shown in FIG. 7, provision may also be made for the wings 34 to be provided with an additional support 96 which, in particular, runs symmetrically along the respective wings 34 on the upper side thereof forming the bearing area 58. This support 96 increases the stability of the wings 34. It also serves as bearing element of the wings 34 against the bearing area 60 of the ring element 64. A larger spacing between the ends 94 of the wings 34 and the ring element 64 is thereby obtained, i.e., the hinged joints 50 can be formed at a larger distance from this ring element 64. In turn, the swivelling capability of the wings 34 is thereby improved.

Provision may also be made for a corresponding support to be arranged only in the area of an end 94 of a wing 34.

Figure 8:
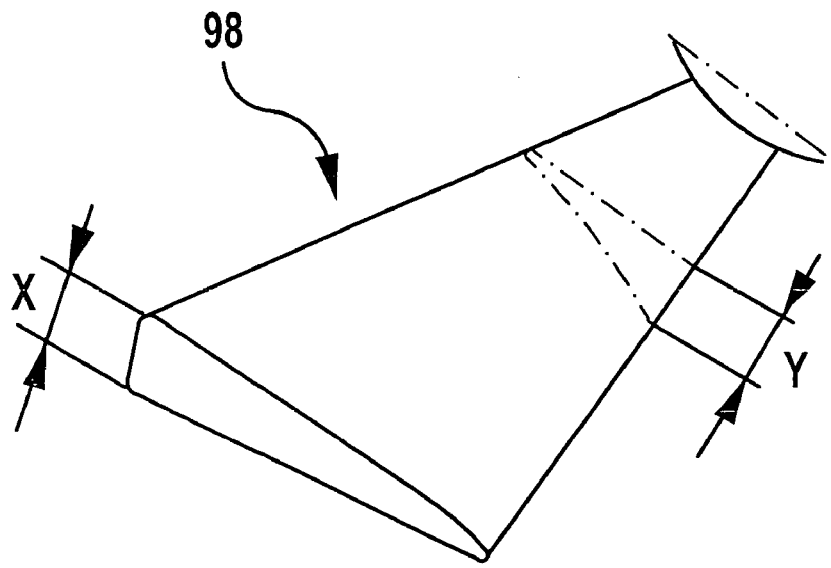
FIG. 8 is a perspective view of a further embodiment of a wing.

As shown in FIG. 8, provision may be made for a wing 98 which is seated for swivelling movement on the closure device 30 to have a height X in its profile cross section at its broader side which corresponds to a curvature height Y at an underside of such a wing 98.

Figure 9:
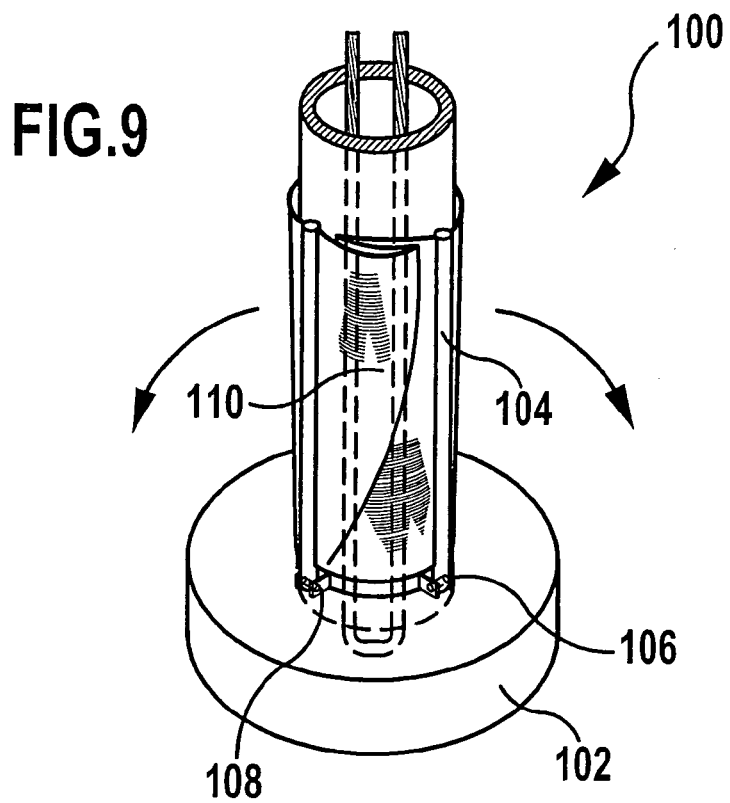
FIG. 9 shows a further embodiment of an inventive closure device in the flapped-in position.
Figure 10:
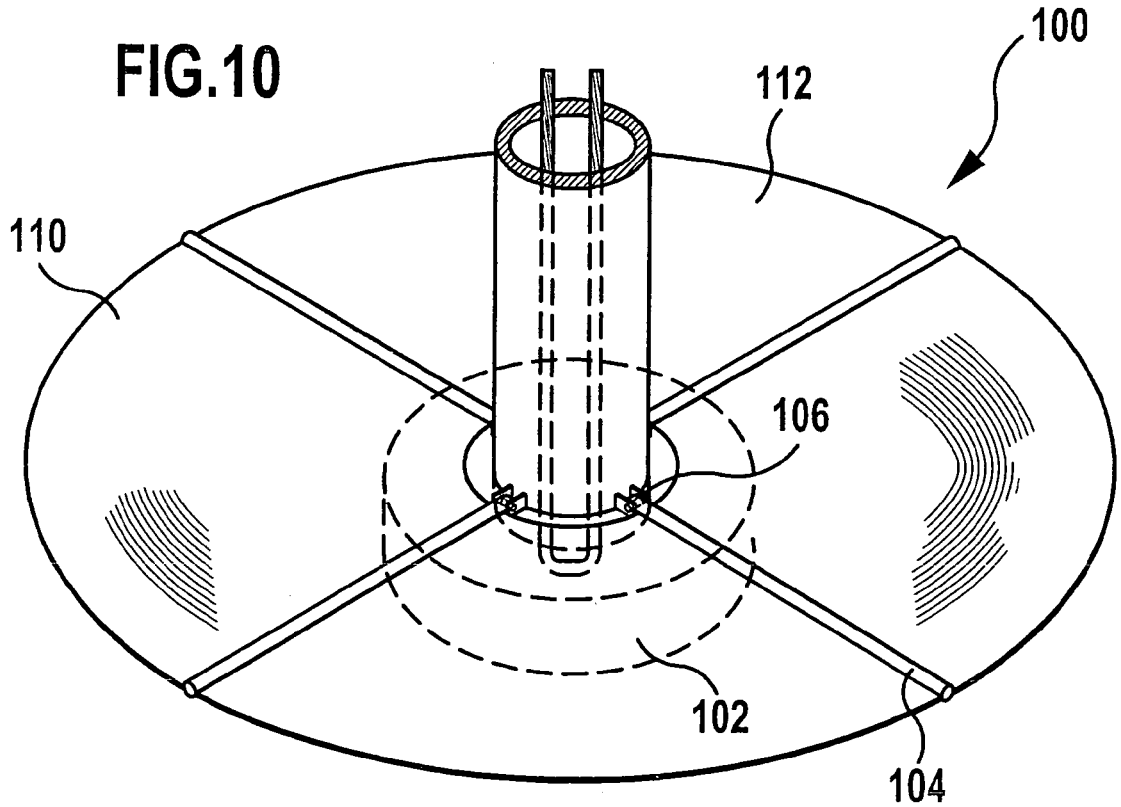
FIG. 10 shows the closure device according to FIG. 9 in the flapped-out position.

In a further embodiment shown in FIGS. 9 and 10, which is generally designated 100, a base part 102 is provided, which is basically of the same design as the above-described base part 32.

A plurality of wings 104 of ridge-shaped design are held on this base part 102. These wings are seated at hinged joints 106 for swivelling movement on the base part 102. The hinged joints 106 may be film hinges. Provision may also be made for the wing 104 or a bearing element 108 for the wing 104 to be provided with stub shafts and for the bearing element 108 or the wing 104 to have shaft receptacles for these stub shafts.

The wings 104 hold bearing elements 110 made of a bendable material and, in particular, a plastic material. The bearing elements 110 provide bearing areas 112 to enable placement of the closure device 100 on tissue in a flapped-out position (FIG. 10). The bearing elements 110 may be spanned between adjacent wings 104. They may be arranged on sides of the adjacent wings 104 which face one another. It is, however, also possible for the bearing elements 110 to be fixed on an upper side of the wings 104.

In a flapped-in position (FIG. 9) the bearing elements 110 are bent in such a way and, in particular, folded in such a way that they do not protrude over the outer circumference of the base part 102. By virtue of the bendability of the material of the bearing elements 110, transition from the flapped-in position to the flapped-out position (FIG. 10) is ensured.

In the flapped-out position, the bearing areas 112 lie substantially at a right angle to the central axis of the base part 102 and form an essentially interruption-free bearing area. When the bearing elements 110 are held on an upper side of the wings 104, this bearing area is also smooth.

The bearing elements 110 are preferably of such design that in the flapped-out position of the wings 104, the bearing areas 112 between adjacent wings 104 are flat.

The bearing elements 110 are arranged, for example, by means of a film hinge connection to the respective wings 104.

The inventive closure device 100 basically operates in the same way as described hereinabove with reference to the first embodiment. With the inventive applicator device, the closure device 100 can be positioned at an opening in tissue which is to be closed. The positioning element associated with the closure device 100 is designed to bring about an unfolding of the wings 104.

FIG. 9 shows the wings 104 in a position in which they lie against a holding mandrel. The bearing elements 110 are preferably of such design that this position can only be reached with the exertion of force. This means that in a position in which force is not exerted, by virtue of the intrinsic elasticity of the bearing elements 110, these move the wings 104 away from the holding mandrel so that the wings 104 lie at a small angle to a central axis of the base part 106. Thus the positioning element of the applicator device can then act on the wings 104 so as to bring about the flapped-out position (FIG. 10).

The invention claimed is:

1. Closure device for an opening in a layer of tissue, comprising:
a plurality of separate wings which provide bearing areas on tissue surrounding the opening; and
a base part;
wherein:
each of the wings are held by means of a respective film hinged joint for swiveling movement on the base part at only end of the closure device;
the joints are fixed on an upper surface of the base part, said upper surface facing the tissue when bearing areas bear on the tissue; and
the wings are arranged for swiveling movement on the base part such that in a flapped-in position neighboring wings have partially overlapping contact with one another such that no part of the wings protrudes laterally over the base part and the arrangement of the wings in the flapped-in position has a circumference which is identical to or smaller than that of the base part.

2. Closure device in accordance with claim 1, wherein swivel axes of the joints are oriented substantially at a right angle to a central axis of the base part.

3. Closure device in accordance with claim 1, wherein swivel axes of the joints lie parallel to tangents to an outer circumference of the base part.

4. Closure device in accordance with claim 1, wherein the wings are held integrally on the base part.

5. Closure device in accordance with claim 1, wherein the wings in an area outside of the associated joints are of substantially rigid design.

6. Closure device in accordance with claim 1, wherein the base part in an area outside of the joints is of substantially rigid design.

7. Closure device in accordance with claim 1, wherein in a flapped-out position, the wings form the bearing areas on the tissue.

8. Closure device in accordance with claim 7, wherein in the flapped-out position, the wings are oriented substantially at a right angle to a central axis of the base part.

9. Closure device in accordance with claim 1, wherein the joints are set back on the base part in relation to a circumferential rim of the base part.

10. Closure device in accordance with claim 1, wherein said plurality of wings comprises at least two wings.

11. Closure device in accordance with claim 1, wherein said plurality of wings comprises diametrically opposed wings.

12. Closure device in accordance with claim 1, wherein the wings are arranged around a circumference of the base part.

13. Closure device in accordance with claim 1, wherein the base part has a round outer cross section.

14. Closure device in accordance with claim 1, wherein a suture thread is held on the base part.

15. Closure device in accordance with claim 1, wherein the base part has spaced openings for a suture thread to pass therethrough.

16. Closure device in accordance with claim 1, wherein in the flapped-in position, the wings extend at an incline to the base part.

17. Closure device in accordance with claim 1, wherein the base part is provided with one or a plurality of bearing areas for the wings, which inhibit swiveling of the wings beyond a bearing position.

18. Closure device in accordance with claim 17, wherein the bearing area or bearing areas on the base part is or are formed on a ring-shaped bearing element.

19. Closure device in accordance with claim 17, wherein the wings comprise a support for placement against the associated bearing areas.

20. Closure device in accordance with claim 1, wherein the wings have a width which increases in a direction away from the base part.

21. Closure device in accordance with claim 1, wherein the base part is provided with a coupling for a holding mandrel.

22. Closure device in accordance with claim 1, wherein the base part comprises a holding element for the wings and a ring element.

23. Closure device in accordance with claim 22, wherein the ring element is held on the holding element by a snap closure.

24. A closure system, said closure system comprising:
a plurality of separate wings which provide bearing areas on tissue surrounding an opening in the tissue; and
a base part;
wherein
each of the wings are held by means of a respective film hinged joint for swiveling movement on the based part at only end of the closed device;
the joints are fixed on an upper surface of the base part, said upper surface facing the tissue when bearing areas bear on the tissue; and
the wings are arranged for swiveling movement on the base part such that in a flapped-in position neighboring wings have partially overlapping contact with one another such that no part of the wings protrudes laterally over the base part and the arrangement of the wings in the flapped-in position has a circumference which is identical to or smaller than that of the base part;
said applicator device comprising:
a positioning element which is longitudinally displaceable in the trocar sheath and by means of which the wings of the closure device are transferable from the flapped-in position in which the closure device is displaceable in the trocar sheath to a flapped-out position;
a holding mandrel for holding and positioning the closure device, said holding mandrel having a hollow interior through which a suture thread is guided; and
a first centering means for centering the positioning element in the trocar sheath;
wherein the positioning element provides a second centering meals for the holding mandrel which substantially prevent transverse movability of the holding mandrel relative to the positioning element.

25. Applicator device for a closure device in accordance with claim 24, wherein the positioning element comprises bearing areas for the wings for swilveling the wings outwading.

26. Applicator device for a closure device in accordance with claim 24, wherein the positioning element surrounds the holding mandrel at least partially.

27. Applicator device for a closure device in accordance with claim 24, wherein the holding mandrel is guided for longitudinal displacement on the positioning element.

28. Applicator device for a closure device in accordance with claim 24, wherein the first centering means comprises one of a reducing sleeve or a set of reducing sleeves for centering the positioning element in the trocar sheath.

* * * * *

UNITED STATES PATENT AND TRADEMARK OFFICE
CERTIFICATE OF CORRECTION

PATENT NO. : 7,311,720 B2
APPLICATION NO. : 10/789372
DATED : December 25, 2007
INVENTOR(S) : Mueller et al.

It is certified that error appears in the above-identified patent and that said Letters Patent is hereby corrected as shown below:

Column 11, line 12: after "only" insert -- one --.

Column 12, between lines 19 and 20 insert:
-- a closure device; and
an applicator device for holding and positioning said closure device;
a trocar sheath adapted to accept the applicator device and the closure device;
said closure device comprising: --.

Column 12, line 23: "wherein" is corrected to read -- wherein: --.

Column 12, lines 25 and 26 are corrected to read:
-- hinged joint for swiveling movement on the base part at only one end of the closure device --.

Column 12, line 49: "meals" is corrected to read -- means --.

Column 12, line 50: "prevent" is corrected to read -- prevents --.

Column 12, line 55: "wading" is corrected to read -- wardly --.

Signed and Sealed this

Thirteenth Day of May, 2008

JON W. DUDAS
*Director of the United States Patent and Trademark Office*